United States Patent [19]

Duggan et al.

[11] Patent Number: 4,895,818

[45] Date of Patent: Jan. 23, 1990

[54] PHOSPHONITE-AND PHOSPHINITE-PROMOTED RUTHENIUM - COBALT CATALYSTS FOR THE DEALKOXYHYDROXYMETHYLATION OF ACETALS TO FORM GLYCOL ETHERS

[75] Inventors: D. Michael Duggan, Drexel Hill; James E. Lyons, Wallingford; Harry K. Myers, Cochranville, all of Pa.; Robert E. Ledley, Hockessin, Del.

[73] Assignee: Sun Refining and Marketing Company, Philadelphia, Pa.

[21] Appl. No.: 238,435

[22] Filed: Aug. 31, 1988

Related U.S. Application Data

[62] Division of Ser. No. 871,351, Jun. 6, 1986.

[51] Int. Cl.$^4$ ............................................. B01J 31/20
[52] U.S. Cl. ................................ 502/161; 502/153; 502/154; 502/155; 502/162
[58] Field of Search ............... 502/153, 154, 155, 161, 502/162

[56] References Cited

U.S. PATENT DOCUMENTS

| | | | |
|---|---|---|---|
| 2,525,793 | 10/1950 | Gresham et al. | 260/615 |
| 4,062,898 | 12/1977 | Dubeck et al | 260/632 |
| 4,308,403 | 12/1981 | Knifton | 568/678 |
| 4,317,943 | 3/1982 | Knifton | 568/678 |
| 4,356,327 | 10/1982 | Knifton | 568/678 |
| 4,357,477 | 11/1982 | Kinfton | 568/678 |
| 4,390,734 | 6/1983 | Knifton | 568/678 |
| 4,408,078 | 10/1983 | VanLeeuwen et al. | 502/169 X |
| 4,617,287 | 10/1986 | Lyons | 502/161 X |
| 4,652,542 | 3/1987 | Duggan et al. | 502/154 |
| 4,663,489 | 5/1987 | Duggan et al. | 502/161 X |
| 4,692,426 | 9/1987 | Duggan et al. | 502/154 |

FOREIGN PATENT DOCUMENTS 034374 8/1981 European Pat. Off. ............ 568/678

OTHER PUBLICATIONS

Chemical Abstracts, 81:83432.

*Primary Examiner*—Patrick P. Garvin
*Attorney, Agent, or Firm*—J. Edward Hess; Donald R. Johnson

[57] ABSTRACT

Ruthenium cobalt- or cobalt-containing catalysts which have been promoted with phosphonites or phosphinites effectively catalyze the dealkoxyhydroxymethylation of aldehyde acetals to form glycol monoethers. Methylal, for example, may be reacted with syngas, i.e., CO and $H_2$, in the presence of these phosphonite- or phosphinite-promoted cobalt or ruthenium- cobalt catalysts to form the monomethyl ether of ethylene glycol. In a like manner acetaldehyde may be converted to the corresponding propylene glycol monoether. The process may advantageously be carried out with high yields and selectivities in the presence of a polar or non-polar organic solvent in combination with the catalyst system of this invention.

The invention is also directed to the phosphonite- or phosphinite-promoted cobalt and ruthenium-cobalt catalyst systems per se.

6 Claims, No Drawings

PHOSPHONITE-AND PHOSPHINITE-PROMOTED RUTHENIUM - COBALT CATALYSTS FOR THE DEALKOXYHYDROXYMETHYLATION OF ACETALS TO FORM GLYCOL ETHERS

This is a division of application Ser. No. 871,351 filed June 6, 1986.

BACKGROUND OF THE INVENTION

1. Scope of the Invention

This invention relates to the dealkoxyhydroxymethylation of aldehyde acetals. More particularly, it relates to a novel process for the dealkoxyhydroxymethylation of certain dialkyl-, dicycloalkyl-, diaryl-or cyclic-aldehyde acetals by reacting said acetals with syngas, i.e., hydrogen and carbon monoxide, in the presence of novel phosphonite- or phosphinite-promoted ruthenium-cobalt catalysts or phosphonite- or phosphinite-promoted cobalt catalyst systems, to form the corresponding glycol monoethers. Still more particularly, it relates to the catalysts per se and methods for preparing the same. In a further embodiment, it is also directed to a process for the dealkoxyhydroxymethylation of acetals in the presence of a solvent in combination with the aforedescribed catalyst system. The acetals described herein may be prepared separately or formed in situ from the corresponding aldehyde and alcohol precursors.

The glycol ethers described herein encompass known classes of compounds having various uses, as for example as jet fuel additives, cleaners, coatings solvents, intermediates in the production of certain diphthalates, and the like.

Description of the Prior Art

One current well-known method of manufacturing glycol monoethers such as monoalkyl ethers consists of reacting ethylene oxide with the alcohol corresponding to the desired alkyl ether, employing various known catalysts systems.

Alternatively, the cobalt-catalyzed reaction of aldehydes or their dialkyl acetals with syngas, i.e., the carbon monoxide-hydrogen mixture, to form the corresponding glycol ether is also described in the art. Thus, for example, a method of making ethylene glycol ethers is described in U.S. Pat. No. 2,525,793 which employs cobalt oxide to catalyze the reaction of methylal with syngas to provide a reaction mixture which, afterhydrogenation over nickel, gives relatively uneconomical conversions on the order of 25–33%.

Numerous attempts have been made to obtain more practical yields of glycol ethers from aldehydes or their dialkylacetals. A number of promoters have been used in conjunction with various cobalt catalysts in an effort to improve reaction rates and product yields. U.S. Pat. No. 4,062,898, for example, discloses a ruthenium chloride-promoted cobalt iodide catalyst which hydrocarbonylates formaldehyde dimethylacetal (methylal) to ethylene glycol monomethyl ether, (EGMME) in yields of 10% or less. The reaction temperature required is 185° at 20 atm. or above. A second method, described in Jpn. Kokai Tokkyo Koho 81 83,432, (1981) uses substantial quantities of 2,4,6-collidine or similar aromatic amines to promote the cobalt carbonyl-catalyzed hydrocarbonylation of methylal in benzene as a solvent. The reaction of methylal with highly pressurized syngas in this process at 190° C. for 10 hours gave 44% selectively to EGMME at 98% conversion. A further patent, Euro. Pat. Appln. EP 34,374 (1981) uses both iodine and triphenyl or tricyclohexylphosphine together with $RuCl_3 \cdot H_2O$, to promote the $Co(Ac)_2 \cdot 4H_2O$ - catalyzed hydrocarbonylation of methylal using 3000 psig of syngas, and temperatures of between 150° and 175° C. to obtain results nearly comparable to those of the Japanese. U.S. Pat. No. 4,346,020 teaches a combination of certain cobalt and ruthenium compounds and a Group VA compound. However, that patent addresses a fundamentally different reaction and it is essential that an additional component be present, e.g. an iodine promoter, for ethanol synthesis from methanol.

More recently, Knifton has found that cobalt carbonyl promoted with a Group VIB donor ligand catalyzes the hydrocarbonylation of an aldehyde in an alcohol to make ethylene glycol monoethers; U.S. Pat. No. 4,308,403. Yields of ethylene glycol monobutyl ether (EGMBE) as high as 61 wt.% were reported in this patent. A cyclopentadienyl-ligated cobalt catalyst is also effective for these reactions giving glycol ethers in up to 54% yield; U.S. Pat. No. 4,317,943.

Propylene glycol monoalkyl ethers are formed by contacting high pressure mixtures of carbon monoxide and hydrogen with either an acetal or an aldehyde and an alcohol using a cobalt catalyst promoted with a tin- or germanium-containing compound; U.S. Pat. No. 4,356,327. Yields of glycol ethers up to 31 wt.% were reported in this patent. Ethylene glycol ethers were also formed from a formaldehyde acetal or formaldehyde and an alcohol using tin or germanium promoters for cobalt carbonyl; U.S. Pat. No. 4,357,477. The highest glycol ether yield (EGMBE) was 53% in this case. Also, propylene glycol monoalkyl ethers were formed by hydrocarbonylation of acetaldehyde acetals or acetaldehyde and alcohols using rhodium, ruthenium or nickel compounds to promote ether cobalt carbonyls or cobalt compounds having group V ligand systems attached. Glycol ether yields up to 28 wt. % were realized when these promoters were used; Knifton, U.S. Pat. No. 4,390,734 (1983).

Finally, earlier filed copending application Ser. No. 783,971, filed Oct. 2, 1985 and now abandoned in the names of Duggan et al, describes the dealkoxyhydroxymethylation of acetals to form glycol ethers using ruthenium-cobalt catalysts which have been promoted with organophosphites. These organophosphite-promoted catalysts, while effective in providing good selectivities at mild operating temperatures, tend to lose their alkoxy groups in exchange reactions with any alcohol which is formed, or with alcohol which is present as a solvent. Over a period of time, the result is a diminution in selectivity of desired product normally obtained by use of these phosphite promoters.

Thus, the use of various promoters, other than the aforedescribed phosphites, for the cobalt-catalyzed hydrocarbonylation of aldehydes or acetals has resulted in glycol ether yields of from 10–61 wt. %, depending on the glycol ether produced. The highest reported yield of EGMME is 44%, of EGMBE is 61% and propylene glycol monoethyl ether, (PGMEE) is 28%. Using the phosphites, yields of up to 92 wt. % have been achieve; however, exchange of the bulky alkoxy groups in the more selective phosphites with product alcohols will degrade their effectiveness as promoters.

SUMMARY OF THE INVENTION

In accordance with the present invention, there is provided an improved process for the reaction of certain dialkyl-, dicycloalkyl-, diaryl-, or cyclic- aldehyde acetals or their aldehyde- alcohol precursors with syngas in the presence of novel phosphonite-and/or phosphinite-promoted ruthenium-cobalt or cobalt catalysts to form the corresponding glycol monoethers. This reaction, which may best be described as the dealkoxyhydroxymethylation of an acetal, formed separately or in situ by the known reaction of an aldehyde with an alcohol, may be depicted by the following general reaction scheme:

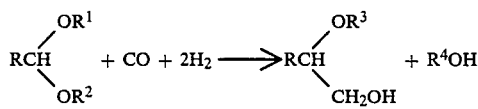

wherein R is hydrogen, alkyl, cycloalkyl, or aryl; $R^1$ and $R^2$, which may be the same or different, are alkyl, cycloalkyl, aryl, and taken together may form a cyclic acetal; $R^3$ is alkyl, cycloalkyl, aryl, or an hydroxy-substituted hydrocarbon moiety; and $R^4$ is alkyl, cycloalkyl, or aryl, corresponding to whichever $R^1$ or $R^2$ group is displaced. In the case where cyclic acetals are employed, however, no alcohol by-product is formed.

Examples of $R^1$, $R^2$, $R^3$ or $R^4$ alkyl, cycloalkyl, and aryl groups which may be employed include those containing such substituted or unsubstituted groups as:

(a) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(b) substituted or unsubstituted cycloalkyl groups, preferably those having from about 5 to about 20 carbon atoms, such as cyclopentyl, cyclohexyl, cycloheptyl, 3-methylcyclopentyl, 3-butyl-cyclohexyl, 3-methylcyclopentyl, 3-butyl-cyclohexyl, cyclooctyl, adamantyl, decalyl, 3-phenylcycloheptyl and the like; and (c) substituted or unsubstituted aryl groups, preferably those having from 6 to about 20 carbon atoms such as benzyl, phenyl, naphthyl, fluoranthyl, tetralyl, tolyl, ethylphenyl, cumyl, anisyl, chlorophenyl, and the like.

It will be understood that when $R^1$ and $R^2$ in the foregoing reaction scheme are different, the resulting products will actually be mixtures of the corresponding glycol ethers and alcohols. It will also be understood, as mentioned above, that $R^1$ and $R^2$ may be joined by one or more bridging atoms to form a cyclic acetal, in which case, under the conditions of this reaction the heterocyclic ring will cleave at a carbon-oxygen bond of the acetal moiety, and hydroxymethylate, thereby forming a dihydroxy compound, i.e. an hydroxy-substituted glycol ether.

The present process, using the novel phosphonite- or phosphinite-promoted catalysts of this invention, provides an improvement over the methods of the prior art in that these catalysts permit the reaction to be carried out under mild conditions of time and temperature, yet most surprisingly provide rates and selectivities of desired product over those obtained by the use of cobalt carbonyl alone, or the ruthenium carbonyls alone or even phosphite-promoted cobalt and/or ruthenium catalyst systems.

In addition to providing high selectivities for the desired glycol ethers, as stated above the phosphonite and phosphinite promoters advantageously reduce exchange reactions with any alcohols present in the reaction medium and are further characterized in being easily synthesized, thereby reducing the cost of the catalyst, and allowing for the preparation of diverse phosphorus-containing structures. Moreover, to the extent that any exchange reactions between the promoters and alcohols present do take place, there is no reduction in selectivity, as is the case with phosphite promoters.

This invention is also directed to the novel phosphonite-and/or phosphinite-promoted ruthenium-cobalt or cobalt catalysts per se, and to methods for preparing them. As described in further detail below, this catalyst system comprises a combination of:

(a) a promoter of the formula

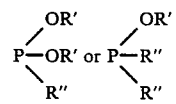

or mixtures thereof, wherein R' and R'', each of which may be the same or different, comprise any organic moieties which are inert to the conditions of the reaction, and include:

(1) hydrogen;

(2) straight or branched chain alkyl groups, preferably those having from 1 to about 20 carbon atoms, such as methyl, ethyl, propyl, isopropyl, n-butyl, t-butyl, 2-ethylhexyl, dodecyl, and the like;

(3) substituted or unsubstituted cycloalkyl groups, preferably those having from about 5 to about 20 carbon atoms, such as cyclopentyl, cyclohexyl, cycloheptyl, 3-methylcyclopentyl, 3-butylcyclohexyl, cyclooctyl, adamantyl, decalyl, 3-phenylcycloheptyl and the like; and (4) substituted or unsubstituted aryl groups, preferably those having from 6 to about 20 carbon atoms such as benzyl, phenyl, halophenyl, perhalophenyl, preferably fluoro-or perfluorophenyl, naphthyl, fluoroanthryl, tetralyl, tolyl, ethylphenyl, cumyl, anisyl, and the like;

wherein the R' groups when other than hydrogen, may, when taken together, form a cyclic compound such as $C_6H_5P(OCH_2)_2$; and (b) a ruthenium-cobalt metal cluster compound, such as $Co_2Ru(CO)_{11}$, $HRuCo_3(CO)_{12}$, or the like; or (c) a mixture of cobalt-containing compounds and ruthenium-containing compounds, wherein said compounds are described in detail below; or (d) the aforesaid cobalt-containing compounds alone, i.e., without ruthenium-containing compounds being present.

The cobalt-containing compounds which may be used in admixture with ruthenium-containing compounds in component (c), above, or alone, as defined in component (d) above, include cobalt oxides, salts, carbonyl derivatives and the like. Examples of cobalt oxides include $Co_2O_3$, $Co_3O_4$, $CoO$; cobalt salts include salts of mineral acids such as cobalt nitrate, cobalt chloride, cobalt sulfate, as well as salts of organic carboxylic acids such as cobalt acetate, cobalt naphthenate, cobalt benzoate and the like. Additionally, other cobalt-containing compounds which may be employed include compounds wherein cobalt is coordinated by anionic ligands derived from beta-diketones, such as cobalt (II)

acetylacetonate and analogs thereof; carbonyl compounds such as dicobalt octacarbonyl, hexacobalt hexadecacarbonyl, $Co_6(CO)_{16}$ and the like, and derivatives thereof obtained by reaction with ligands, including phosphonites and phosphinites as described above. Also, cobalt carbonyl halides and organometallic compounds obtained by reacting cobalt carbonyl compounds with unsaturated organic species such as olefins, acetylene compounds, allylic compounds, such as cyclopentadienyl cobalt dicarbonyl, may likewise be used.

Ruthenium-containing compounds which may be used as co-catalysts with the above cobalt-containing compounds include ruthenium oxides such as ruthenium(IV)oxide hydrate, anhydrous ruthenium(IV)dioxide and ruthenium(VIII)tetraoxide; salts of mineral acids such as ruthenium(III)chloride hydrate or its anhydrous form, and ruthenium nitrosyl nitrate; salts of organic carboxylic acids, such as $Ru_2(OAc)_4(OH)_2(H_2O)_2$ and the like; and salts of anions from organic diketones, such as ruthenium(III)acetylacetonate and ruthenium(III)hexafluoroacetylacetonate and derivatives and analogs thereof. Additionally, there may be employed such compounds as ruthenium carbonyl compounds or hydride derivatives such as $Ru_3(CO)_{12}$, $H_2Ru_4(CO)_{13}$ and $H_4Ru_4(CO)_{12}$, as well as substituted carbonyl species such as those made by the addition of phosphonites and phosphinites and unsaturated organic compounds such as olefins, acetylene compounds and allylic compounds, examples of which are biscyclopentadienylruthenium, $Ru(C_5H_5)_2$, and dichloro(cycloocta-1,5-diene)ruthenium(II); and ruthenium compounds which have any combination of the above ligands and ions, including aromatic ligands such as hexamethylbenzene.

Of particular interest for use as component (c) above are mixtures of ruthenium and cobalt carbonyl compounds as for example, a mixture of $Co_2(CO)_8$ and $Ru_3(CO)_{12}$, or a mixture of $R^5CCo_3(CO)_{12}$, wherein $R^5$ may be hydrogen; alkyl, preferably $C_{1-12}$ alkyl, and most preferably $C_{1-5}$ lower alkyl; cycloalkyl or alkyl-substituted cycloalkyl, preferably $C_{5-10}$ moieties; cycloalkenyl, preferably $C_{6-12}$ cycloalkenyl, such as cyclohexenyl or cyclooctenyl; alkoxy, preferably $C_{1-12}$ alkoxy, such as methoxy or propoxy; aryl or alkyl-, cycloalkyl-, alkoxy-, halo-, or cyano-substituted aryl, preferably $C_{6-20}$ moieties; or a silyl moiety of the formula $R^6_3Si$, wherein $R^6$ is alkyl or aryl.

Also, of particular interest for use as component (d) above is the aforedescribed carbyne-substituted cobalt carbonyl compound, namely $R^5CCo_3(CO)_9$, wherein $R^5$ is as described above, as for example $HCCo_3(CO)_9$, or the like.

From the foregoing description of the cobalt and ruthenium compounds of components (b), (c) or (d) of the aforedescribed catalyst, it will be seen that a wide range of these materials may be used, whether as mixtures of cobalt and ruthenium compounds, as metal clusters containing both cobalt and ruthenium atoms or as cobalt compounds alone.

DESCRIPTION OF THE CATALYST SYSTEM

The novel catalysts employed in the process of this invention are readily prepared by mixing the phosphonite or phosphinite with any of the cobalt or ruthenium-cobalt compounds or mixtures set forth above. The molar ratio of organophosphite to ruthenium-cobalt compound or mixture, or to cobalt compounds, is desirably in the range of 1:5 to 5:1, and preferably 1:3 to 3:1.

The phosphonite and phosphinite promoters are generally known compounds described in the art. Thus, for example, the phosphonites may be prepared by reacting the dichlorophosphine, $R''PCl_2$, with any of a wide variety of alcohols in the presence of an amine, wherein $R''$ is as defined above. Similarly, the phosphinites may be prepared by reacting the chlorophosphines, $R''_2PCl$, with alcohols, in the presence of an amine, wherein again, $R''$ is as defined above. Examples of such phosphonites or phosphinites include $PhP(OEt)_2$, $PhP(OCH_3)_2$, $Ph_2P(OEt)$, $Ph_2P(OCH_3)$, $PhP(OCH_2)_2$, $PhP(OBu)_2$, $C_5F_5P(OEt)_2$, and the like, of which $PhP(OEt)_2$ and $PhP(OBu)_2$ are preferred, wherein Ph is phenyl, Et is ethyl, and Bu is butyl. Cyclic phosphonites may be prepared in a similar fashion, but using more dilute conditions.

The aforedescribed ruthenium and cobalt compounds are also generally well-known compounds described in the art. Of particular interest, for example, are the ruthenium carbonyl dicobalt octacarbonyl mixtures, more specifically, triruthenium dodecarcarbonyl-dicobalt octacarbonyl mixtures. This mixture, for example, may readily be prepared by simply mixing dicobalt octacarbonyl ($Co_2(CO)_8$) with ruthenium dodecarcarbonyl ($Ru_3(CO)_{12}$) in the reaction medium, together with the phosphonite or phosphinite. The molar ratios of the ruthenium to cobalt compounds in the catalyst are optimally in the range of about 10:1 to 1:10, and preferably about 5:1 to 1:5.

The metal cluster $Co_2Ru(CO)_{11}$ may be prepared by the method disclosed by Roland et al, *Angew. Chem. Int. Ed. Engl.*, 20, 679 (1981). The carbyne-substituted cobalt carbonyl compounds, $R^5CCo_3(CO)_9$, wherein $R^5$ is as defined above, may be prepared in accordance with the procedures taught in *Inorganic Synthesis*, Wiley-Interscience Pub., New York Vol. 20, #53-B, pp. 226 et seq. (1980). As indicated above, this catalyst may be used with the phosphonite or phosphinite promoter with or without a ruthenium compound, but more preferably with the ruthenium component. The molar ratios of these two components in the latter combination, should optimally be in the range of about 10:1 to 1:10 and preferably about 5:1 to 1:5.

DESCRIPTION OF THE PROCESS

The acetal dealkoxyhydroxymethylation reaction with syngas, as described above, utilizing the novel phosphonite- or phosphinite-promoted ruthenium-cobalt or cobalt catalysts of this invention, may conveniently be conducted in a generally known manner whereby the desired acetal is reacted with syngas under elevated temperature and pressures for given periods of time, during which period the reaction mixture is actively stirred. In this reaction, the volume ratio of carbon monoxide to hydrogen in the syngas desirably is in the range of from about 1:5 to 5:1, and more preferably 1:3 to 3:1. Following rapid cooling, the reaction product is then recovered from the mixture in a routine manner.

In contrast to the published prior art reaction conditions described above, the catalysts of this invention advantageously permit the use of mild operating conditions. Thus, temperatures in the range of from about 100° to 200° C., and preferably about 125° to 175° C., pressures of from about 500 to 5000 psi, and preferably about 1000 to 3000 psi, may satisfactorily be employed. The reaction time is not critical and may range up to several hours, desirably about 1–6 hours.

The weight ratio, in grams, of catalyst to acetal, is desirably in the range of from about 1:1000–1:10, and preferably in the range of from about 1:100–1:10 in a batch reaction.

In a further embodiment of this invention, it has been found that highly advantageous effects may also be obtained in this dealkoxyhydroxymethylation process by the use of solvents with the acetal. The solvents which may be advantageously used comprise any polar or non-polar organic solvents which are inert to the conditions of the reaction.

There may also be employed as solvents $C_{1-12}$ alcohols, such as methanol, ethanol, butanol, 3-ethyl-2-hexanol and the like; ethers which will not cleave under the conditions of the reaction, such as glyme, diglyme, diphenyl ether and the like; aromatics and substituted aromatics such as benzene, toluene, xylene, chlorobenzene, dichlorobenzene, anisole, and the like.

The solvents may be employed in amounts of up to 90 volume percent of the reaction mixture, and preferably in amounts of about 20 to 80 percent.

In still a further embodiment of this process, it has been found that with acylic acetals, when the reaction is carried out in an excess of an alcohol solvent, wherein the ratio of acetal to alcohol solvent is desirably in the range of from about 1:2 to 1:20, and preferably 1:5 to 1:10, and wherein the R group of the alcohol used is different from the $R^1$ and/or $R^2$ substituents on the acetal starting material, these different R groups of the alcohol will, in the course of the reaction, replace the $R^1$ and/or $R^2$ groups on the acetal in a substitution reaction, thereby resulting in a glycol monoether in which the R group of the ether moiety corresponds to the R group of the alcohol solvent.

This reaction may be illustrated by the following equation:

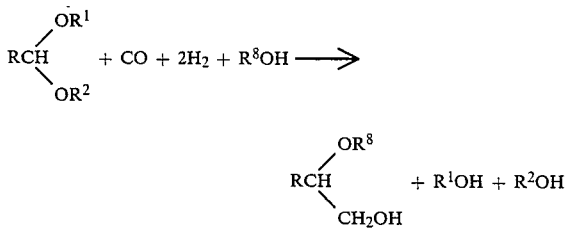

wherein R, $R^1$, and $R^2$ are as defined above, except that cyclic acetals are not included, and $R^8$ is a different alkyl, cycloalkyl, or aryl group than $R^1$ and/or $R^2$, and desirably has from 1 to about 20 carbon atoms. Depending upon the length of the time the reaction is allowed to continue, intermediate mixtures of higher and lower molecular weight substituents on the acetal corresponding to both those of the $R^1$ and/or $R^2$ groups and those of the alcohol solvent will be found in the reaction product.

The acetal starting materials employed in this invention have the aforedescribed general formula, namely

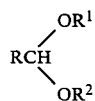

wherein the R, $R^1$ and $R^2$ are as defined above. These acetals can be prepared in a known manner, as for example as described in E. V. Dehmlav and J. Schmidt, Tetrahedron Letters, p. 95–6 (1976) B. S. Bal and H. W. Pinnick, J. Org. Chem. V44 (21), p. 3727–8(1979) D. W. Hall, U.S. Pat. No. 3,492,356, Jan. 27 (1970), by the reaction of an aldehyde such as formaldehyde with an alcohol, or mixture of alcohols, of the general formula $R^1OH$ or $R^2OH$, where again $R^1$ and $R^2$ are as defined above, to form the corresponding acetal. In the case of cyclic acetals, the alcohol must be a diol. Hereinafter, when the acetal is referred to, it will be understood that the corresponding precursors, i.e., the desired aldehyde and alcohol, are also intended to be included.

As mentioned above, the $R^1$ and $R^2$ substituents of the acetal may comprise a bridging group to form such cyclic acetals as

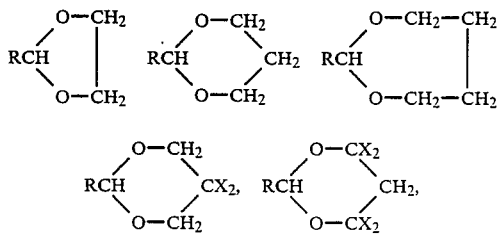

and the like, wherein R is defined above, and wherein X is selected from the group consisting of alkyl, aralkyl, aryl and cycloalkyl groups, preferably those having from 1 to about 20 carbon atoms. As described above, cleavage of the ring under the conditions of this reaction will result in the formation of the corresponding hydroxy-substituted glycol ether.

Illustrations of products thus formed from cyclic acetals include, for example, diethylene glycol from dioxolane, the conversion of 2-or 4-methyldioxolane to the corresponding hydroxy glycol ether and the like.

It is important, in selecting the acetal starting material, that it not contain any substituents which would adversely affect the reaction. In other words, the R, $R^1$ and $R^2$ groups should not, for example, contain such reactive moieties as arsine, amino, sulfido or carbonyl groups, acetal moieties, or olefins or acetylenic triple bonds. Other like groups will be recognized or readily determined by those skilled in the art as resulting in products other than the desired monoethers. On the other hand, halogen, alkoxy, and hydroxy moieties and the like may be present on the hydrocarbon substituents without adverse effect.

When these acetals are dealkoxyhydroxymethylated with syngas in accordance with the process of this invention, there is obtained the corresponding glycol monoether in which the ether moiety will correspond to the $R^1$ and $R^2$ groups of the acetal starting material. Also formed in lesser amounts are a tri-substituted ethane of the general formula

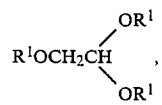

wherein $R^1$ (or, alternatively, $R^2$ or mixtures of $R^1$ and $R^2$) is as defined above, which may be recycled to form additional acetal starting material, and alcohol by-products. Again, as above, if the $R^1$ and $R^2$ groups of the acetal are different, a mixture of corresponding R-substituted compounds will result. This tri-substituted ethane is believed to form during the reaction from an alkoxyacetaldehyde, e.g., the intermediate methoxyacetaldehyde, when methylal is used, ethoxyacetaldehyde when ethylal is used, and the like.

As shown below, the selectivities for the desired monoether over the tri-substituted by-product are in the ratio of from about 3:1 to as much as 10:1 or more.

In a preferred embodiment of this invention, the starting materials are preferably symmetrical acetals where the $R^1$ and $R^2$ groups are lower alkyl groups of 1 to about 4 carbon atoms, thereby forming the corresponding ethylene glycol mono-lower alkyl ethers such as the monomethyl ether, the monoethyl ether, the monobutyl ether, and the like.

Alternatively, the acetal may contain such $R^1$ and $R^2$ groups as naphthyl and phenyl. In the case of naphthyl, the reaction, e.g., of the formaldehyde acetal with syngas will provide 2-(2-naphthyloxy) ethanol, a known sedative, which in turn may be oxidized to the corresponding 2-naphthyloxyacetic acid, a plant growth hormone.

Likewise, the dealkoxyhydroxymethylation of, e.g., the formaldehyde acetal wherein $R^1$ and $R^2$ are phenyl will produce 2-phenoxy-ethanol, a topical antiseptic, which when oxidized results in phenoxyacetic acid, a fungicide. Similarly, the formaldehyde acetal wherein $R^1$ and $R^2$ are 2,4,5-trichlorophenyl will yield 2,4,5-trichlorophenoxyacetic acid, an herbicide. In a like manner, when $R^1$ and $R^2$ are p-nonylphenyl, p-nonylphenoxyacetic acid, a corrosion inhibitor and antifoaming agent in gasoline and cutting oils will be formed.

Each of the aforesdescribed products may be recovered routinely by methods well known in the art.

The invention will now be illustrated by, but is not intended to be limited to, the following examples.

EXAMPLES 1-19

A series of runs was carried wherein butylal and acetal, $(CH_3CH(OC_2H_5)_2)$, respectively, were reacted with syngas in the presence of various catalyst combinations, as shown in Tables I and II below under reaction conditions described in the footnotes of these tables. The yields, selectively and conversion for each reaction is reported in these tables; the results show the effectiveness of phosphonite and phosphinite promoters for ruthenium and cobalt catalysts compared to related catalyst systems.

TABLE I
EFFECTS OF PHOSPHONITE PROMOTERS ON THE REACTION OF SYNGAS WITH BUTYLAL TO GIVE ETHYLENE GLYCOL MONOBUTYL ETHER[a]

| Example | Promoter[b] (mmoles) | Yield(%)[c] | Selectivity(%)[d] | Conversion(%) |
|---|---|---|---|---|
| 1 | — | 58 | 59 | 98 |
| 2 | PPh₃ (3.0) | 62 | 78 | 78 |
| 3 | TNPP (3.0) | 75 | 80 | 94 |
| 4 | DEPP (3.0) | 80 | 82 | 97 |
| 5 | DBPP (3.0) | 79 | 83 | 95 |
| 6 | DBPP (1.5) | 83 | 85 | 97 |
| 7 | DEPP (3.0)[e] | 80 | 86 | 93 |

[a]Unless otherwise noted, all reactions were run in a 300 ml stainless steel rocking autoclave using 8.38 g butylal, 19.47 g o-dichlorobenzene, 1.18 g mesitylene (as internal standard), 800 psi CO, and 1600 psi H₂ at 150° C. for 5 hours. The Ru and Co catalysts employed in each reaction were 0.5 mmole of HCCo₃(CO)₉ and 1.3 mmole of Ru₃(CO)₁₂.
[b]PPh₃ = triphenylphosphine (comparative example); TNPP = trineopentylphosphite (comparative example); DEPP = diethylphenylphosphonite; DBPP = dibutylphenylphosphonite.
[c]Values for ethylene glycol monobutyl ether in percent relative to butylal added. Analyses performed by gas chromotography of reaction solutions using a 50-meter Supelcowax-10 capillary column.
[d]Selectivity = (yield/conversion) × 100.
[e]This reaction was run using 400 psi CO and 800 psi H₂.

TABLE II
EFFECTS OF PHOSPHONITE AND PHOSPHINITE PROMOTERS ON THE REACTION OF SYNGAS WITH ACETAL TO GIVE PROPYLENE GLYCOL MONOETHYL ETHER[a]

| Example | Promoter[b] (mmoles) | Yield (%)[c] | Selectivity (%)[d] | Conversion (%) |
|---|---|---|---|---|
| 8 | — | 27 | 29 | 94 |
| 9 | PPh₃ (3.0) | 22 | 27 | 81 |
| 10 | TNPP (3.0) | 32 | 35 | 92 |
| 11 | DEPP (3.0) | 34 | 38 | 90 |
| 12[e] | DEPP (6.0) | 46 | 48 | 94 |
| 13 | DBPP (3.0) | 36 | 39 | 92 |
| 14 | DBPP (1.5) | 39 | 40 | 96 |
| 15 | MDPPI (3.0) | 30 | 35 | 85 |
| 16 | MDCHPI (3.0) | 40 | 42 | 93 |
| 17 | IPDCHPI (3.0) | 38 | 42 | 92 |
| 18 | IPDPPI (3.0) | 27 | 31 | 88 |
| 19 | PFPDBPO (3.0) | 31 | 32 | 96 |

[a]Unless otherwise noted, all reactions were run in a 300 ml stainless steel rocking autoclave using 8.37 g acetal (1,1-diethoxyethane), 19.47 g o-dichlorobenzene, 1.18 g mesitylene (as internal standard), 800 psi CO, and 1600 psi H₂ at 150° C. for five hours. The Ru and Co catalysts employed in each reaction were 0.5 mmole HCCo₃(CO)₉ and 1.0 mmole of Ru₃(CO)₁₂.
[b]PPh₃ = triphenylphosphine (comparative example);
TNPP = trineopentylphosphite (comparative example);
DEPP = diethylphenylphosphonite;
DBPP = dibutylphenylphosphonite;
MDPPI = methyldiphenylphosphinite;
MDCHPI = methyldicyclohexylphosphinite;
IPDCHPI = isopropyldicyclohexylphosphinite;
IPDPPI = isopropyldiphenylphosphinite;
PFPDBPO = parafluorophenyldibutylphosphonite.
[c]Values for propylene glycol monoethyl ether in percent relative to acetal added; corrected for handling losses using the mesitylene internal standard. Analyses performed by gas chromotography of reaction solutions using a 50-meter Supelcowax-10 capillary column.
[d]Selectivity = (yield/conversion) × 100.
[e]This reaction was run using 0.67 mmoles HCCo₃(CO)₉, 6.0 mmoles Ru₃(CO)₁₂, 102.9 g o-dichlorobenzene, 9.35 g acetal, 1000 psi CO, and 2100 psi H₂, with 1.18 g of mesitylene.

A comparison of the results of comparative examples 1 and 2, and 8 and 9 of Tables I and II respectively, with the remaining examples of this invention will show that in almost all cases, the all-important measure of yield and selectivity for desired product are higher when the phosphonite and phosphinite promoters of this invention are employed with the Ru and Co catalysts.

What we claim is:

1. In a catalyst useful in dealkoxyhydroxymethylation of acetals and which contains a metal selected from the group consisting of cobalt and both ruthenium and cobalt, the improvement wherein said catalyst additionally contains a promoter of the formula

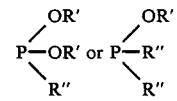

or mixtures thereof, wherein R' and R'', each of which may be the same or different, are hydrogen, alkyl, cycloalkyl, or aryl; and wherein the R' groups, when other than hydrogen, may, when taken together, form a cyclic compound.

2. Catalyst according to claim 1 wherein said metal is cobalt.

3. Catalyst according to claim 2 wherein said cobalt is cobalt carbonyl.

4. Catalyst according to claim 1 wherein said metal is both cobalt and ruthenium.

5. Catalyst according to claim 4 wherein said cobalt and ruthenium are cobalt carbonyl and ruthenium carbonyl.

6. Catalyst according to any one of claims 1-5 wherein the promoter is PhP(OEt)₂, PhP(OCH₃)₂, Ph₂P(OEt), Ph₂P(OCH₃), PhP(OCH₂)₂, PhP(OBu), or C₅F₅P(OEt)₂, wherein Ph is phenyl, Et is ethyl, and Bu is butyl.

* * * * *